(12) United States Patent
Sheehan et al.

(10) Patent No.: US 6,386,314 B1
(45) Date of Patent: May 14, 2002

(54) FLEXIBLE EARPHONE ASSEMBLY FOR USE DURING HEARING SCREENING

(75) Inventors: Neil J. Sheehan, Palo Alto; Christian Walton, Belmont; David Sheraton, Irvine, all of CA (US); Toshibumi Wakayama, Tokyo (JP); William New, Jr., Woodside, CA (US)

(73) Assignee: Natus Medical, Inc., San Carlos, CA (US)

( * ) Notice: Subject to any disclaimer, the term of this patent is extended or adjusted under 35 U.S.C. 154(b) by 0 days.

(21) Appl. No.: 09/395,799

(22) Filed: Sep. 14, 1999

(51) Int. Cl.$^7$ .............................................. E04G 1/00
(52) U.S. Cl. ........................ 181/129; 181/130; 181/135
(58) Field of Search ................................. 181/129, 130, 181/135; 128/864, 866, 867; 381/310, 371, 372, 373

(56) References Cited

U.S. PATENT DOCUMENTS

| | | | |
|---|---|---|---|
| 2,570,675 A | 10/1951 | Heflin | 128/151 |
| 2,684,067 A | 7/1954 | Lienard | 128/152 |
| 2,802,214 A | 8/1957 | Hanks | 2/209 |
| 3,117,575 A | 1/1964 | Carrell et al. | 128/152 |
| 3,841,325 A | 10/1974 | Pickard | 128/151 |
| 4,308,623 A | 1/1982 | Voorhees | 2/174 |
| 4,616,643 A | 10/1986 | Jung | 128/151 |
| 4,669,129 A * | 6/1987 | Chance | 2/209 |
| 4,713,843 A * | 12/1987 | Duncan | 2/209 |
| 4,930,520 A * | 6/1990 | Livernai | 128/746 |
| 5,826,582 A * | 10/1998 | Sheehan et al. | 128/164 |
| 5,826,852 A | 10/1998 | Sheehan et al. | 128/864 |
| 6,151,717 A * | 11/2000 | Lindgren et al. | 2/209 |

\* cited by examiner

Primary Examiner—Robert E. Nappi
Assistant Examiner—Kim Lockett
(74) Attorney, Agent, or Firm—Orrick, Herrington & Sutcliffe LLP (57) ABSTRACT

An earphone assembly is disclosed that includes an annular baffle having an outer surface and an inner surface as well as an interior wall and an exterior wall. The interior wall defines a central chamber. A transparent, flexible lid is attached to the baffle along the outer surface, completely covering the central chamber and forming an acoustic seal with the baffle. The lid has an inner face and an outer face. The flexibility of the earphone is improved by creating hinges in the lid and by providing cuts, or other discontinuities, in the baffle. For example, a radial cut may be disposed in the annular baffle. Further, a circumferential cut may also (or alternatively) be disposed in the baffle, extending from the inner surface and disposed between the exterior wall and the interior wall. At least one hinge may be disposed on the flexible lid. To improve the attachment of the earphone to the patient's head, tabs are mounted to the exterior wall. An adhesive material is applied to the inner surface of the annular baffle and to the tabs, thereby increasing the adhesive surface compared to existing earphones. A proprietary connection may be employed such that the baffle sends out an identifying signal to the transducer. The transducer then controls its transmission of acoustic energy based upon the identifying signal. In certain instances, the transducer may stop sending acoustic energy at all if it does not recognized the signal from the baffle.

56 Claims, 5 Drawing Sheets

FLEXIBLE EARPHONE ASSEMBLY FOR USE DURING HEARING SCREENING

FIELD OF THE INVENTION

The present invention relates generally to earphones which cover the ear, and more particularly to earphones for infants for use in hearing screening tests.

BACKGROUND OF THE INVENTION

It is known to conduct tests to identify hearing impairments in humans (also known as "hearing screening"). It is critical and advantageous to determine whether or not any hearing impairments exist at an early age, such as in newborns and infants. This is because the earlier a problem is diagnosed and therapy undertaken, the more likely the therapy or other intervention will minimize the potential problems and costs associated with the identified hearing impairments or loss.

Over the years, hearing screening techniques have been developed which inject a sound input into the ear and detect a response to that input. The response is related to the characteristics of the sound input, the conditions inside the ear, the vibration transmission mechanism of the ear and the neural pathway through to the brain. The response can be analyzed to assess the hearing of the patient.

In many cases, and in particular in the case of infants, hearing screening is performed by using an earphone having a cavity that fits closely about the ear. Auditory tones or "clicks" are fed into the earphone cavity, and the response generated by the patient's ear and the neural activity system in response to the auditory tones is sensed by a transducer. The transducer may be, for example, a microphone, suitable electrodes, an electroencephalogram (used in auditory brainstem response tests), piezo electric materials and like devices that read signals representative of the response to the auditory input. These signals are then processed and the result (as well as the detected signals, if desired) can be displayed on a monitor or other viewing device for analysis of the patient's hearing.

A common problem using this method is that ambient noises are capable of interfering with the stimulus or the response signals, and, thus, the result. In most cases, the monitoring equipment has mechanisms, such as microphones, for detecting and compensating for ambient background noise. However, compensating for noise inside the cavity is difficult. This difficulty is compounded when the earphones do not adhere fully to the skin surface of the patient's head. Any "pulling away" from the head can create a gap which, in turn, may result in "leakage" of acoustic energy. Such leakage may effect any testing. Further, the earphone must be precisely placed on the head of the patient such that the cavity is centered over the ear or the measured response may not be accurate.

Another concern when testing the hearing of children is the delivery of the acoustic energy. Damage to the ear can result if too much acoustic energy is delivered. Typically, the transducers commonly employed to deliver this acoustic energy are designed to work in combination with the earphone assembly and deliver a controlled amount of acoustic energy. However, when earphones are used in combination with other transducers, the resultant acoustic energy is less certain and thus may be too high, causing damage to the ear.

U.S. Pat. No. 4,930,520 to Liverani, incorporated herein by reference, provides a disposable earphone for testing the hearing in infants which includes a toroidal baffle of anechoic, insulative foam, a rigid clear planar window plastic sheet adhered to one side of the baffle defining a cavity, and an adhesive coating on the other side of the baffle for temporarily bonding the disposable earphone to the region surrounding the infant's ear. The earphone is capable of being used with transducers for transferring acoustical energy to the infant's ear for testing. The Liverani device has been commercialized and is sold under the trademark EAR COUPLERS® disposable earphones by Natus Medical Incorporated, the assignee of this invention.

U.S. Pat. No. 5,826,582 to Sheehan et. al., incorporated herein by reference, relates to an earphone assembly for use with a hearing screener particularly suitable to test infants for hearing impairment. The earphone includes a generally D-shaped reusable cover formed of a rigid material. The cover has a back wall, a side wall extending from the perimeter of the back wall to define a cavity, a port in the cover to receive a transducer, and a generally D-shaped disposable element that is adhesively coated on two sides to be secured to the cover and to the patient's head. The cover may have a notch located along the perimeter of the re-usable body for removing the disposable element. A liner is used to cover the disposable element adhesive sides to protect them from contamination during packaging and prior to use. The disposable element may have a die cut so that a portion of it can be removed to make the earphones adjustable for infants with large ears.

One difficulty with existing earphone assemblies is that the baffles or covers must deform to match the contour of the patient's head. In particular, near the jaw, the patient's head is naturally contoured and does not present a flat mating surface for the earphones. When using a compressible, elastic material for the baffle, internal shear stresses are created between adjacent portions of the baffle since these portions will be compressed or stretched different amounts. As the material seeks to return to its original shape, certain portions of the baffle may be pulled off the patient's head, creating a "leak" for acoustic energy. This problem is exacerbated by the rigid plates employed as lids that transfer the pull to the baffle material. While earphones can be formed to match the contour of a particular patient's head, this may be inordinately expensive and may require custom earphones for each patient and earphones designed specifically for either the left or right ear.

Thus, although the aforementioned prior art devices are useful in hearing screening there remains a need for an improved earphone that overcomes the inadequacies of the known devices and, further, provides advances that improves the attenuation of ambient and external noise inside the cavity of the earphone. In particular, an inexpensive device for readily and accurately matching the head contour without resulting in a substantial loss in acoustic energy during testing is required.

OBJECTS AND SUMMARY OF THE INVENTION

Accordingly, it is an advantage of an aspect of the instant invention to provide an earphone assembly capable of flexing to better match the contours of the patient's head.

It is an advantage of another aspect of the invention to provide an earphone assembly that is capable of being used with ears of different sizes and for either the left or the right ear.

It is an advantage of another aspect of the invention to provide an earphone assembly that is generally insulated from external noise.

It is yet an advantage of another aspect of the invention to provide an earphone assembly that includes a visual grid or target to assist caregivers in positioning the earphone about the ear during hearing screening tests.

It is an advantage of yet another aspect of the invention to provide an earphone assembly that includes a flexible lid cooperating with a flexible baffle to fit snugly on the heads of patients of various sizes.

It is an advantage of yet another aspect of the invention to provide an earphone assembly with an increased adhesive area for better securement to a patient's head.

It is an advantage of yet another aspect of the instant invention to provide an earphone assembly that is flexible and yet inexpensive to manufacture.

It is an advantage of yet another aspect of the instant invention to provide an earphone assembly that delivers consistent acoustic energy during a hearing test.

In accord with one aspect of the invention, an earphone is provided that includes an annular baffle having an outer surface and an inner surface separated by a height as well as an interior wall and an exterior wall separated by a thickness. The interior wall defines a central chamber. A transparent, flexible lid is attached to the baffle along the outer surface, completely covering the central chamber and forming an acoustic seal with the baffle. The lid has an inner face and an outer face. The flexibility of the earphone is improved by creating hinges in the lid and by providing cuts, or other discontinuities, in the baffle. For example, a radial cut may be disposed in the annular baffle. Further, a circumferential cut may also (or alternatively) be disposed in the baffle, extending from the inner surface and disposed between the exterior wall and the interior wall. At least one hinge may be disposed on the flexible lid. To improve the attachment of the earphone to the patient's head, tabs are mounted to the exterior wall. An adhesive material is applied to the inner surface of the annular baffle and to the tabs, thereby increasing the adhesive surface compared to existing earphones.

In accord with another aspect of the invention, an earphone assembly is provided for use with a transducer for hearing screening. An annular baffle includes an outer surface and an inner surface separated by a height. The baffle defines a central chamber. A flexible lid is attached to the baffle along the outer surface and covering the central chamber. An aperture extends through the baffle to the central chamber for conveying acoustic energy to and from the chamber. The flexible lid permits the baffle to more readily conform to the patient's head.

Certain implementations of this aspect of the invention may provide any combination of the following features: the flexible lid includes an inner face and an outer face, a hinge is disposed along a face of the flexible lid and an acoustic seal is formed between the inner face of the lid and the outer surface of the baffle; the hinge is a groove disposed in the outer face of the flexible lid; the lid includes an inner face and outer face and a plurality of hinges are disposed in the outer face of the lid; at least two grooves intersect; at least two grooves intersect at an angle of about 70°; the flexible lid is transparent and a target is positioned on the lid; the annular baffle includes a first upper quadrant, a second upper quadrant, a first lower quadrant and a second lower quadrant, and the hinge extends generally from the first upper quadrant to the second lower quadrant; at least two grooves extend parallel to each other; at least one cut is disposed in the annular baffle extending from the inner surface at least partly through the height of annular baffle; the annular baffle comprises four contiguous quadrants and cuts are positioned between at least three quadrants, extending radially outward from the central chamber; the annular baffle has an exterior wall and an interior wall separated by a thickness, and a circumferential cut extends at least partly through the thickness of the annular baffle from the inner surface disposed between the exterior wall and the interior wall; radial slits extend at least partly through the annular baffle; the annular baffle further comprises an interior wall defining the central chamber, and an exterior wall, and that the assembly further comprises tabs mounted to the exterior wall and an adhesive applied to the inner surface of the annular baffle and the tabs; the baffle has an interior wall with an oval shape defining the central chamber, an exterior wall having a rectangular shape and an adhesive applied to the inner surface of the annular baffle.

In accord with another aspect of the invention, an earphone assembly is provided for use during hearing screening. A baffle forms a closed loop and defines a central chamber. The baffle has an inner surface, an outer surface, an interior wall and an exterior wall. A lid is attached to the outer surface of the baffle. Means are provided for conveying sound to the central chamber disposed in the wall. At least one cut is disposed in the baffle to improve the ability of the baffle to conform to the patient's head.

Certain implementations of this aspect of the invention may provide any of combination of the following features: the cut comprises at least one slit disposed along the exterior wall of the baffle, extending circumferentially about the baffle; the cut is disposed along the interior wall of the baffle, extending circumferentially about the central chamber; the cut extends radially from the interior wall to the exterior wall; tabs are mounted to the exterior wall; means are provided for increasing the flexibility of the lid; the flexibility increasing means comprises at least one hinge disposed on the lid; the hinge is a groove extending from the first upper portion of the wall to the second lower portion of the wall; the flexibility increasing means comprises a plurality of grooves disposed on the lid, the lid is made of a substantially transparent material and the grooves form a visible grid; a slot is disposed along an interior wall of the baffle extending circumferentially about the central chamber and the lid is seated on the slot; a visible translucent target is positioned on the lid; the cut comprises a circumferential cut extending at least partly through the thickness of the annular baffle from the inner surface and disposed between the exterior wall and the interior wall; the cut comprises radial slits extending at least partly through the annular baffle; a first set of radial slits extend from the inner wall to the circumferential cut and a second set of radial slits extend from the circumferential cut to the outer wall; the first set of radial slits are offset from the second set of radial slits; the lid has an edge which is disposed on the outer surface between the interior wall and the exterior wall; a corner formed by the outer surface and the exterior wall is beveled; a corner formed by the inner surface and the exterior wall is beveled; a corner formed by the inner surface and the interior wall is beveled.

In accord with yet another aspect of the invention, an earphone assembly is provided having a baffle that forms a closed loop. The baffle has an inner surface, an outer surface, an interior wall, an exterior wall, a thickness extending from the interior wall to the exterior wall and a height extending from the inner surface to the outer surface. The interior wall defines a central chamber having an oval shape. A flexible lid is attached to the outer surface of the baffle, covering the central chamber and forming an acoustic seal with the outer surface of the baffle. Means are provided for conveying sound to the central chamber disposed in the baffle. A cut is disposed in the baffle. The cut in the baffle and the flexible lid cooperate to allow the earphone assembly to conform to the patient's head.

Certain implementations of this aspect of the invention may provide any combination of the following features: the lid is cup-shaped with a concave surface surrounded by a lip which itself is attached to the outer surface of the baffle by an adhesive such that the concave surface faces the baffle; a slot is disposed in the outer surface of the baffle and the lip is seated in the slot; a step is formed in the outer surface of the baffle and the lip is seated snugly about the step; and the lip is contoured to approximate the contour of the patient's head.

In accord with another aspect of the invention, an earphone is provided for attachment to skin of a patient undergoing hearing screening. An annular baffle includes an outer surface and an inner surface separated by a height as well as an interior wall and an exterior wall separated by a thickness. The interior wall defines a central chamber. Means are provided for covering the chamber and forming an acoustic seal with the outer surface of the annular baffle. Means are provided for increasing the flexibility of the baffle. Means are provided for conveying acoustic energy to the chamber. Means are provided for increasing the flexibility of the covering means. Means are provided for forming an acoustic seal between the inner surface of the annular baffle and the skin of the patient.

Certain implementations of this aspect of the invention may provide any combination of the following features that: the baffle flexibility increasing means comprises at least one radial cut in the annular baffle extending at least partly through the annular baffle; the covering means comprises a lid and the means for increasing the flexibility of the covering means comprises at least one groove disposed on the lid.

In accord with another aspect of the invention, an earphone assembly is provided. A baffle forms a closed loop and has an inner surface, an outer surface, an interior wall, and an exterior wall. A thickness extends from the interior wall to the exterior wall. A height extends from the inner surface to the outer surface. The interior wall defines a central chamber. A cup-shaped lid with a concave surface is surrounded by a lip. The lip is attached to the outer surface of the baffle such that the concave surface faces the baffle. Means disposed in the baffle are provided for conveying sound to the central chamber.

Certain implementations of this aspect of the invention may provide any combination of the following features: a slot is disposed in the outer surface of the baffle and the lip is seated in the slot; a step is formed in the outer surface of the baffle wherein the lip is seated snugly about the step.

In accord with another aspect of the invention, an earphone assembly for use with a transducer for hearing screening is provided. An annular baffle includes an outer surface and an inner surface separated by a height, and an interior wall and an exterior wall separated by a thickness. The interior wall defines a central chamber. A lid is attached to the baffle along the outer surface and covering the central chamber. An aperture extends through the baffle to the central chamber for conveying acoustic energy to the chamber. Tabs are attached to the exterior wall of the annular baffle.

In accord with another aspect of the invention, an earphone assembly is provided for use with a transducer for hearing screening. The assembly includes an annular baffle having an outer surface and an inner surface separated by a height, and an interior wall and an exterior wall separated by a thickness. The interior wall defines a central chamber. A transparent lid is attached to the baffle along the outer surface, completely covering the central chamber and forming an acoustic seal with the baffle. The lid has an inner face and an outer face. At least one cut extends at least partly through the annular baffle. An adhesive material applied to the inner surface of the annular baffle.

Certain implementations of this aspect of the invention provide that: a circumferential cut is disposed in the outer surface of the annular baffle; a proprietary connection is disposed between the annular baffle and the transducer; a means is provided for sending a signal identifying the baffle mounted in the baffle and a means are provided for reading the identifying signal operably engaged to the transducer to determine the identity of the baffle; a means is provided for controlling the transducer based, at least in part, upon the identifying signal; the identifying means comprises a computer chip mounted in the baffle; the proprietary connection comprises an aperture in the baffle having a non-circular cross-section designed to match the non-circular cross-section of the transducer.

In accord with another aspect of the invention, a method is provided for assembling an earphone for use with a transducer for hearing screening. An annular baffle is provided including an outer surface and an inner surface separated by a height. A central chamber is defined within the baffle. A flexible lid is attached to the baffle along at least a portion of the outer surface. The central chamber is covered with the flexible lid. A port is provided through the baffle to the central chamber for conveying acoustic energy to and from the chamber. Certain implementations of this aspect of the invention provide that cuts are inserted into the baffle and the hinges are provided on the lid.

BRIEF DESCRIPTION OF THE DRAWINGS

Further features of the invention, its nature, and various advantages will become more apparent from the accompanying drawings, and the following detailed description of the invention, in which like reference numerals refer to like elements, and in which.

DETAILED DESCRIPTION OF THE DRAWINGS

Figure 1:
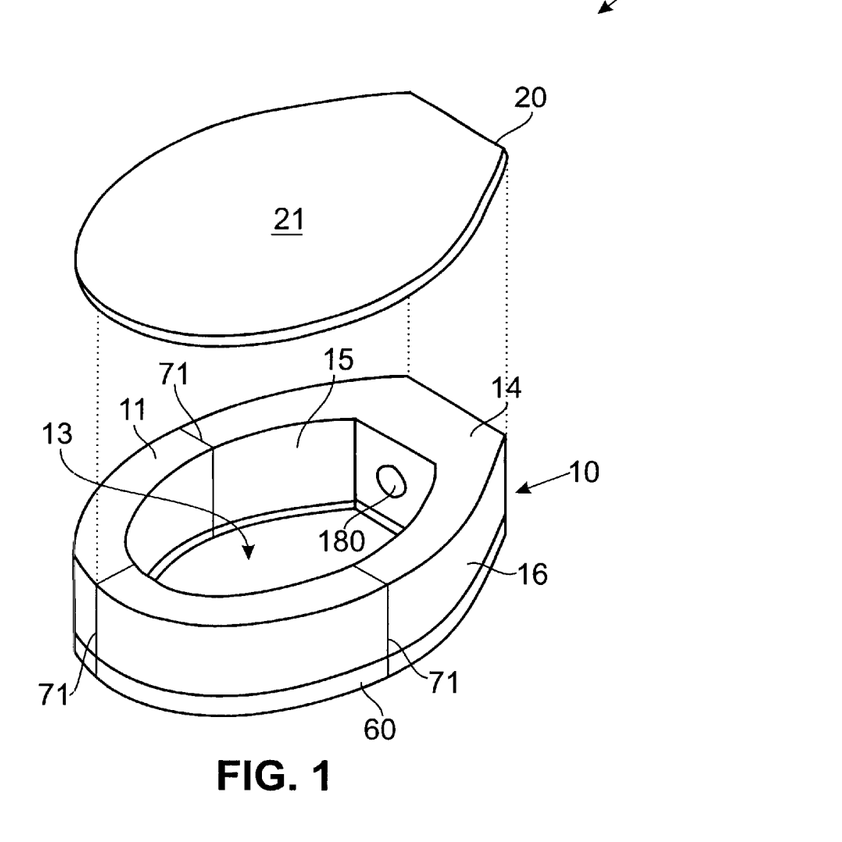
FIG. 1 is a perspective, exploded view of an earphone assembly in accord with an embodiment of the instant invention.
Figure 2:
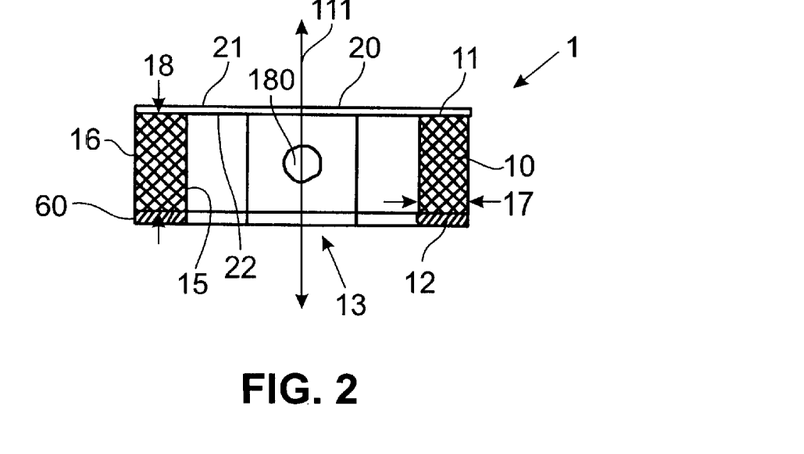
FIG. 2 is a cut-away end view of the earphone assembly of FIG. 1.

Referring to FIGS. 1 and 2, the earphone assembly 1 of the present invention includes a lid 20 attached to a baffle 10. Preferably, an acoustic seal is formed between the lid and the baffle. The baffle may be generally D-shaped or toroidal. However, the baffle may have various shapes and still practice the invention. In particular, the baffle may have a generally oval shape with a flattened end 14 (see also FIGS. 3–8). This flattened end includes an aperture or a port 180 that is particularly adapted to receive a transducer. An adapter or other port designed to receive the transducer could also be employed, as one skilled in the art would appreciate. As discussed more fully below, a proprietary interface may be incorporated into the port such that it will mate and cooperate only with a transducer designed for that particular port. This ensures control of the sound level to the baby is maintained by employing validated components. Preferably, the baffle is formed of a compressible material, such as an elastomer foam, which can be readily compressed to fit snugly against the head of a patient. Other acceptable baffle materials include other foams, low durometer rubbers, pneumatic bladders, and the like.

The baffle 10 includes an interior wall 15 and an exterior wall 16 separated by a thickness 17. The interior wall of the baffle defines a central chamber 13 that is completely covered by the lid 20. The baffle also includes an outer surface 11 and an inner surface 12 separated by a height 18. The lid 20 has an inner face 22 and an outer face 21. Preferably, the outer surface of the baffle is flat to match the contour of the flat inner face of the lid 20. It will be appreciated that the outer surface can be curved or compliant to match the contour of the lid if the lid is not flat.

An adhesive layer 60 is disposed along the inner surface 12 of the baffle 10. The adhesive layer secures the baffle to the head of the patient. A removable slip or release liner (not shown) can be supplied over the adhesive until it is ready for use. As currently preferred, the inner surface 12 of the baffle 10 is flat. It will be appreciated that the inner surface could be contoured, as disclosed in U.S. Pat. No. 5,826,582, incorporated herein by reference, and still practice the invention. However, this has not been found to be necessary.

Referring to FIGS. 3–8, cuts or slits 71–80 are positioned in the baffle 10 in order to increase the flexibility of the baffle, allowing it to better match the profile of the patient's head. The cuts allow portions of the baffle to compress and stretch different amounts without transferring shear stress to adjacent portions of the baffle. Preferably, the cuts extend nearly completely through the baffle from the inner surface 12 toward the outer surface 11. It will be appreciated that in certain applications, the cuts can be less extensive, extending only a short way into the baffle from the inner surface. Further, the cut may extend completely through the baffle, effectively separating portions of the baffle, and still practice the invention. Any combination of cut depths can be employed; or the cuts may be angled, effectively deeper near the inner face and less deep near the outer face. While it is preferred that the cut extend from the inner surface, it will be appreciated that the cut can be disposed entirely between the inner surface and the outer surface, or extend inward from the outer surface partly through the baffle, and still practice the invention. The cut should be thin enough so that the adjacent portions of the baffle touch, thereby minimizing "leaking" of the acoustic energy through the cut. Of course, if desired, a filler material can be provided between the adjacent portions, filling any gap created by the cuts.

Figure 3:
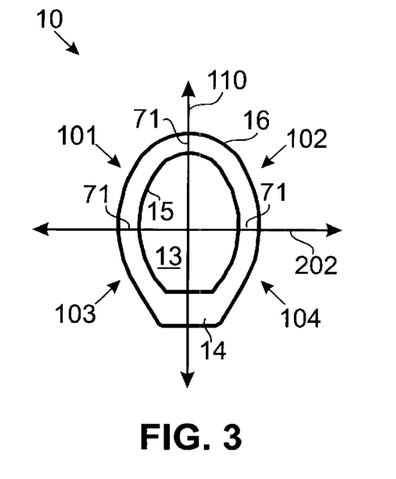
FIG. 3 is a bottom view of a baffle for use with the assembly of FIG. 1 with cuts separating the quadrants.

Referring specifically to FIGS. 1 and 3, the baffle 10 includes four portions or quadrants: a first upper quadrant 101, a second upper quadrant 102, a first lower quadrant 103 and a second lower quadrant 104 defined by a vertical axis 110 and a horizontal axis 202. Cuts 71 are positioned on the borders between the two upper quadrants 101 and 102, and between the respective upper and lower quadrants. The cuts extend completely through the baffle substantially radially out of the central chamber 13, from the interior wall 15 to the exterior wall 16. As used herein, cuts which extend perpendicular to a normal on the exterior wall of the baffle are deemed to extend substantially radially out of the central chamber. Although, in this embodiment, the cuts effectively separate adjacent portions of the baffle, the portions are maintained in position because they are each secured to the lid 20. Consequently, adjacent portions of the baffle are in contact, preventing leakage of acoustic energy.

Figure 4:
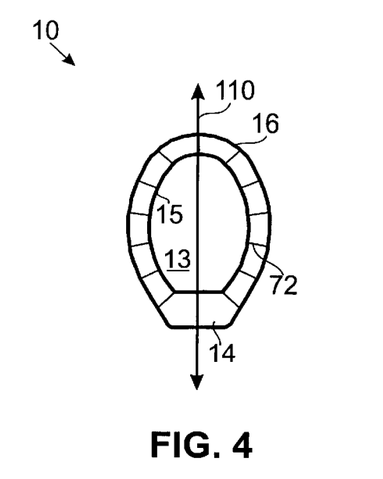
FIG. 4 is a bottom view of a baffle for use with the assembly of FIG. 1 with radial cuts.
Figure 4A:
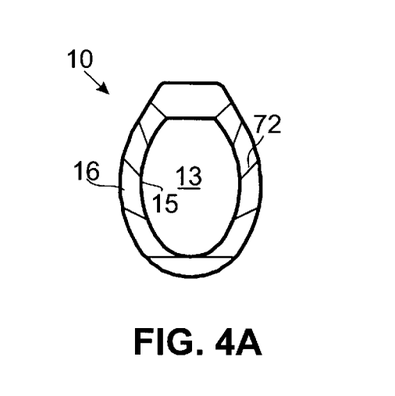
FIG. 4A is a bottom view of a baffle for use with the assembly of FIG. 1 with angled cuts.

Referring specifically to FIG. 4, numerous slits or cuts 72 are provided in the baffle 10 extending completely through the baffle substantially perpendicular to the tangent on the exterior wall 16 out of the central chamber 13, from the interior wall 15 to the exterior wall 16. As shown, thirteen cuts are provided which are disposed symmetrically about a central vertical axis 10. One skilled in the art will appreciate that any number of cuts may be employed. Further, the cuts can be supplied at regular or irregular (not shown) distances. For example, the cuts may be supplied at closer intervals to correspond to more severe curvature in the patient's head (such as near the mastoid) or more cuts may be provided in the baffle remote from the aperture 180. While the cuts are shown extending substantially tangent to the exterior wall, it will also be appreciated that the cuts may be angled and/or curved to better match the typical contour of a patient's head or may simply extend radially from the central chamber. Referring to FIG. 4A, the cuts may be disposed at an angle with respect to a radius and still practice the invention. It is believed that the angled cuts shown in FIG. 4A will reduce leakage of acoustic energy compared to cuts extending radially since there will be no straight path from the center of the chamber to the exterior of the baffle. One skilled in the art would appreciate that the cuts could be arranged as desired for a particular application and still practice the invention.

Figure 5:
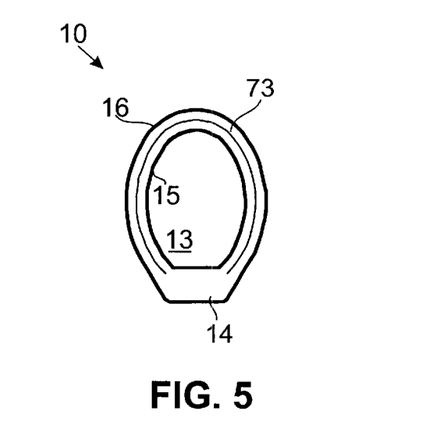
FIG. 5 is a bottom view of a baffle for use with the assembly of FIG. 1 with a circumferential cut.

Referring to FIG. 5, a circumferential cut 73 is disposed in the baffle 10. The circumferential cut extends substantially parallel to the inner wall 15 and the outer wall 16 of the baffle along a mid-point between the two. The circumferential cut extends from one side of the flattened end 14 of the baffle, completely around the baffle to the other side of the flattened end. It will be appreciated that the circumferential cut may be disposed along a limited portion of the baffle, such as extending only along one quadrant. Further, the circumferential cut may extend completely around the baffle, including the flattened side. Currently, this is not preferred in view of the risk to the integrity of the junction between the aperture 180 in the baffle and the transducer. The circumferential cut may extend nearer the inner wall or the outer wall, as may be appropriate based upon the typical contour of the patient's head. Further, several circumferential cuts may extend, either in parallel and/or at differing portions of the baffle, as a particular application would dictate. One advantage of the embodiment shown in FIG. 5 is that the cut does not extend from the central chamber 13 to the exterior or the baffle thereby reducing the likelihood of leakage of acoustic energy through the cut.

Figure 6:
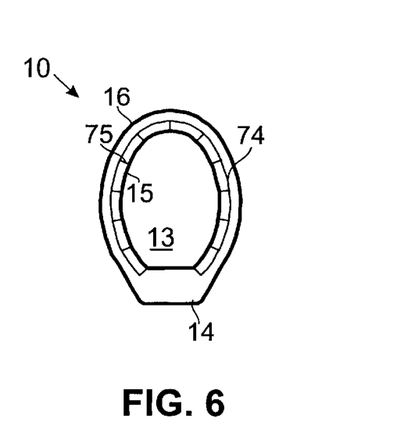
FIG. 6 is a bottom view of a baffle with circumferential and radial cuts extending from the central chamber for use with the assembly of FIG. 1.

Referring to FIG. 6, a circumferential cut 74 extends from one side of the flattened end 14 of the baffle 10 to the other side. Radial cuts 75 extend from the inner wall 15 to the circumferential cut 74. This arrangement permits flexing of adjacent portions of the baffle proximate to the central chamber 13. However, the portion of the baffle near the exterior wall 16 is not broken with cuts and thus reduces any leakage of acoustic energy.

Figure 7:
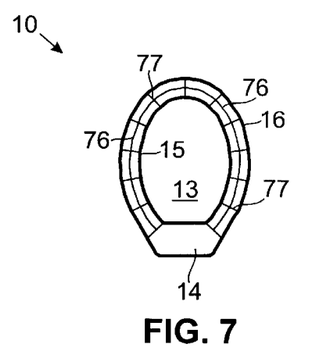
FIG. 7 is a bottom view of a baffle with circumferential and aligned radial cuts extending from the central chamber and from the outer wall for use with the earphone assembly of FIG. 1.

Referring to FIG. 7, a circumferential cut 76 extends from one end of the flattened end 14 of the baffle 10 to the other end. Radial cuts 77 extend completely through the baffle from the inner wall 15 to the outer wall 16. This arrangement provides substantial flexibility, allowing adjacent portions of the baffle to move with respect to each other without transferring shear forces either radially or circumferentially to the adjacent portions. This arrangement would be relatively inexpensive to manufacture but may result in the loss of acoustic energy due to the radial cuts based, in part, on the severity of the contours of the patient's head. However, the "double layer" of this embodiment may act to plug any gaps in a given radial cut.

Figure 8:
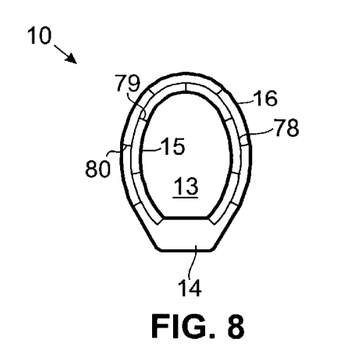
FIG. 8 is a bottom view of a baffle with circumferential and staggered radial cuts extending from the central chamber and from the outer wall for use with the assembly of FIG. 1.

Referring to FIG. 8, a circumferential cut 78 extends from one side of the flattened end 14 of the baffle 10 to the other side. A first set of radial cuts 79 extend from the inner wall 15 to the circumferential cut 78. A second set of radial cuts 80 extend from the circumferential cut 78 to the outer wall 16. The first set and second set of circumferential cuts are staggered or offset such that no radial cut extends directly from the central chamber 13 to the exterior of the baffle. This embodiment may be relatively more expensive to manufacture in view of the more complex arrangement of the cuts. However, the staggered arrangement of radial cuts is believed to reduce the likelihood of acoustic energy leakage since no direct path is formed between its central chamber 13 and the exterior of the baffle, and the sections of baffle ID are maintained in contact by the lid 20.

The lid 20 is preferably flexible, allowing the lid to bend, better matching the contour of the patient's head (and thus exerting less of a pulling force on the baffle 10). Various techniques can be employed to increase the flexibility of the lid. In particular, the lid can be made flexible by forming the lid of a flexible material, by including hinges, or a combination of both. Preferably, the flexible lid is at least somewhat elastic allowing the caregiver to manipulate the lid while positioning the baffle 10. However, it should not be so rigid that it cannot flex easily to match the contour of the patient's head. Preferably, the acoustical impedance of the lid should be higher than that of the external air. Currently, it is preferred that the lid be made of a flexible, transparent low durometer material such as PVC. Of course, other materials such as polypropylene or PETG can be employed and still practice the invention.

Figure 9:
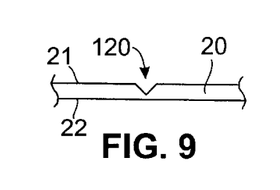
FIG. 9 is a side view in isolation of a hinge for use with the assembly of FIG. 1.
Figure 10:
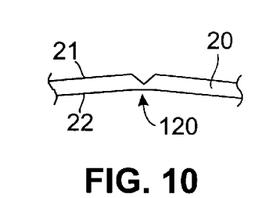
FIG. 10 is a side view in isolation of the hinge of FIG. 9 in a bent condition.

Referring to FIGS. 9 and 10, a hinge 120 is disposed in the lid 20. As currently preferred, the hinge is a groove disposed along the outer face 21 of the lid. The reduced thickness encourages the lid to bend about the groove, as seen in FIG. 10. The groove may also be disposed along the inner face 22 of the lid as well and still practice the invention. Further, other hinge mechanisms may be employed. For example, the lid may be flexed along the hinge before attachment to the baffle. This "pre-flexing" or fatiguing of the lid creates a local weakness, causing the lid to bend along that line more readily. Further, the lid may be made of composite materials. A more flexible material can be disposed along the hinge region while a more rigid material forms the remainder of the lid. In this way, the lid has a desired level of rigidity but is still capable of flexing about the hinge.

Figure 11:
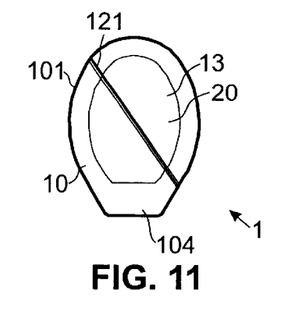
FIG. 11 is a top view of an embodiment of the assembly of FIG. 1 including a single hinge in the lid.

Referring to FIG. 11, a single hinge 121 is disposed in the outer face 21 of the lid 20, extending from a first upper quadrant 101 to a second lower quadrant 104 (see FIG. 3 for reference to the quadrants). On the ear, it is preferred that the hinge 121 extends from the upper rear corer to the lower front corner. The earphone assembly depicted is intended for the right ear. As shown, the hinge cuts through the center point 111 of the central chamber 13. It may be desirable to dispose the hinge somewhat off center, and to orient the hinge at a different angle with respect to the baffle 10, as one skilled in the art would appreciate. This embodiment is relatively inexpensive to manufacture. However, since it employs a single, angled hinge, it is specifically intended for the right ear. Consequently, a corresponding earphone assembly can be provided for the left ear.

Figure 12:
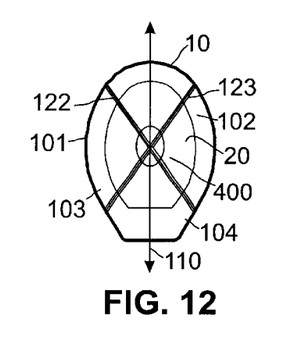
FIG. 12 is a top view of an embodiment of the assembly of FIG. 1 including two angled hinges in the lid and a target on the lid.

Referring to FIG. 12, two hinges 122, 123 are disposed in the outer face 21 of the lid 20. The first hinge 122 extends from a first upper quadrant 101 to a second lower quadrant 104. The second hinge 123 extends from a second upper quadrant 102 to a first lower quadrant 103. The hinges are symmetrical about the vertical axis 110 of the baffle. This arrangement is particularly usefull since the earphone assembly can be used with either the left ear or the right ear. A translucent target 400 (see also FIG. 14) is provided on the lid to assist the caregiver in positioning the baffle on the patient's ear. It will be appreciated that the target may have other shapes (such as a bullseye, a cross, etc.) and still practice the invention.

Figure 13:
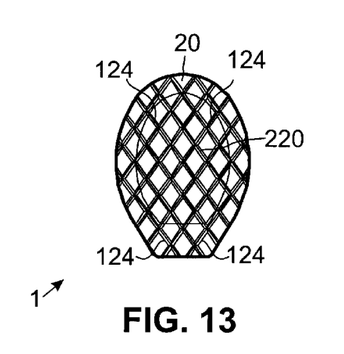
FIG. 13 is a top view of an embodiment of the assembly of FIG. 1 including a plurality of hinges in the lid forming a diamond grid.

Referring to FIG. 13, a plurality of parallel hinges 124 is disposed on the outer face 21 of the lid 20. The use of numerous hinges permits the lid to flex easily along numerous lines. Similar to the embodiment shown in FIG. 12, this embodiment may be used equally well with either the left or the right ear. The crosshatch pattern of the hinges 124 in the embodiment in FIG. 13 (as well as FIG. 15, discussed below) provides a grid 220 for the caregiver to align the center of the chamber 13 with the center of the patient's ear. Thus, the grid acts as a target. A circular translucent target 400 (see FIGS. 12 and 14) or other means for registering the earphone assembly can also be provided on the lid to assist the caregiver in positioning the baffle on the patient's ear.

Figure 14:
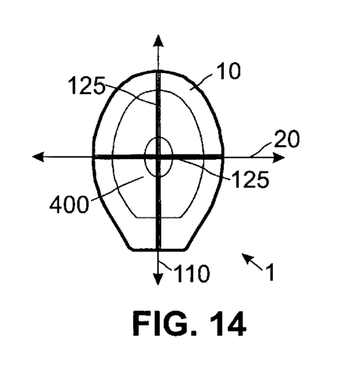
FIG. 14 is a top view of an embodiment of the assembly of FIG. 1 including two hinges in the lid intersecting at right angles.
Figure 15:
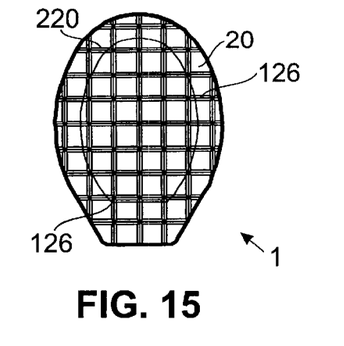
FIG. 15 is a top view of an embodiment of the assembly of FIG. 1 including a plurality of hinges in the lid intersecting at right angles and forming an orthogonal grid.

Referring to FIG. 14, hinges 125 are disposed in the lid 20 along the vertical 110 and horizontal axes 202 of the baffle 10. Referring to FIG. 15, a plurality of hinges 126 parallel to either the horizontal axis 202 or vertical axis 110 are provided. Again, this provides a useful grid 220 for the physician to observe the position of the earphone assembly during testing. Both the embodiments shown in FIG. 13 and in FIG. 15 provide numerous hinges that improve the overall flexibility of the lid. While it is currently believed that the embodiment shown in FIG. 13 will best fit the typical patient's head, the caregiver may wish to select a particular lid hinge arrangement depending upon the particular contour of a given patient's head.

Figure 16:
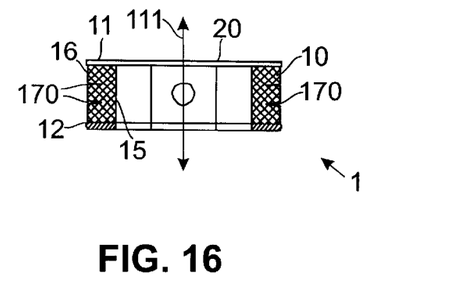
FIG. 16 is an end view in cut-away of an embodiment of the assembly of FIG. 1 including cuts in the outer wall.

Additional flexibility in the baffle 10 may be provided in a direction parallel to the central axis 111 (see FIGS. 2 and 16) of the baffle by providing additional cuts or slits or other convolutions in the foam. Referring to FIG. 16, cuts 170 may be disposed in the baffle, extending from the outer wall 16 parallel to the outer surface 11 and the inner surface 12. As shown in FIG. 16, two horizontal cuts are positioned symmetrically between the inner surface and the outer surface. These cuts extend only partly through the baffle. It will be appreciated that a single cut or greater number of horizontal cuts may be employed. The horizontal cuts may be positioned along the interior wall 15 of the baffle or at different height along the baffle. Further, the cuts may be angled (from the outer wall to the inner wall, from the upper portion to the lower portion, etc.) or staggered.

Figure 17:
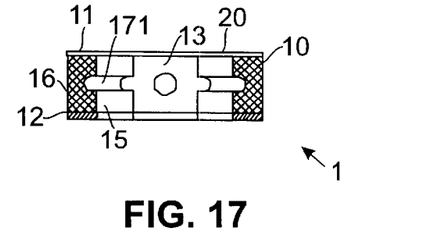
FIG. 17 is an end view in cut-away of an embodiment of the assembly of FIG. 1 with a groove in the inner wall.
Figure 17A:
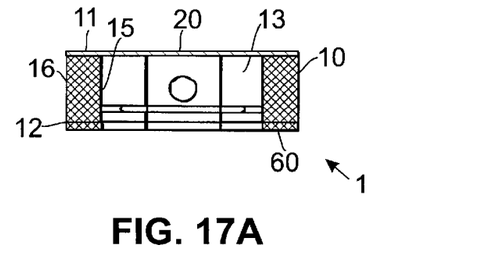
FIG. 17A is also an end view in cut-away of an embodiment of the assembly of FIG. 1 with the groove positioned on the inner wall near the inner surface.
Figure 17B:
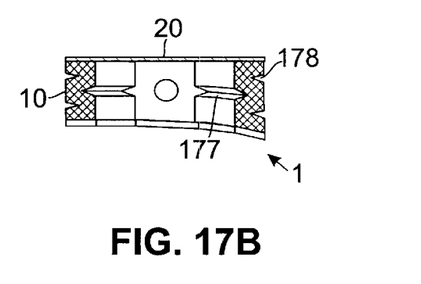
FIG. 17B is also an end view in cut-away of an embodiment of the assembly of FIG. 1 with cuts positioned on the outer wall and a groove positioned on the inner wall between the cuts.

Referring to FIG. 17, a cut or gouge 171 is disposed along the interior wall 15 of the baffle 10, extending from one side of the flattened end 14 to the other side. The gouge has a U-shaped profile but other profiles could be employed and still practice the invention. In FIG. 17A, the gouge has a reduced cross-sectional area is disposed proximate to the inner surface 12 and extends completely about the interior wall of the baffle. Of course, other sizes and positions could be employed and practice the invention. In particular, referring to FIG. 17B, cuts 178 may be positioned on the outer wall while a groove 177 is positioned on the inner wall between the cuts. This arrangement provides and "accordion" effect, allowing the baffle great flexibility.

Figure 18:
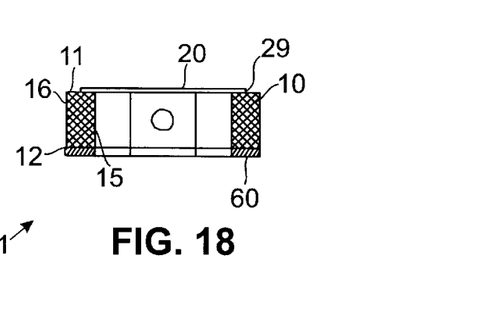
FIG. 18 is an end view in cut-away of an embodiment of the assembly of FIG. 1 wherein the lid is attached to only a portion of the outer surface of the baffle.
Figure 18A:
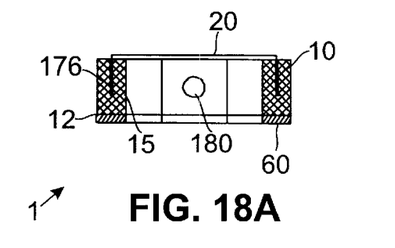
FIG. 18A is an end view in cut-away of an embodiment of the assembly of FIG. 1 wherein the lid is attached to only a portion of the outer surface of the baffle and cuts are positioned in the outer surface of the baffle, adjacent to the edge of the lid.

Altering the attachment between the lid and the baffle can increase the flexibility of the earphone assembly 1. Referring specifically to FIG. 18, the lid 20 is attached to the outer surface 11 of the baffle 10. The edge 29 of the lid 20 is positioned between the outer wall 16 and the inner wall 15. Since the lid does not attach completely to the outer surface of the baffle, there is inherently more flexibility. Further, the lid exerts less of a pulling face on the baffle, particularly at the outer wall. In another embodiment shown in FIG. 18A, cuts 176 are disposed in the outer surface 11 of the baffle, just beyond the edge of the lid. The lid thus exerts a force only on the portion of the baffle proximate to the central chamber 13. However, due to the cut, this force is not translated to the portion of the baffle near the outer wall 16. This further increases the ability of the baffle (or at least portions thereof) to move independent of the lid. Consequently, the lid will exert less of a pulling force on the inner surface 12 of the baffle.

Figure 19:
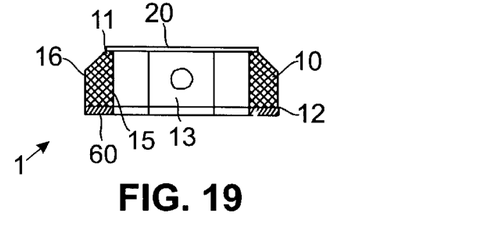
FIG. 19 is an end view in cut-away of an embodiment of the assembly of FIG. 1 wherein the outer top corner of the baffle is beveled.

Referring to FIG. 19, the corner of the baffle 10 formed by the outer wall 16 and the outer surface 11 is beveled. The lid is thus not attached to the baffle for the entire thickness. The reduction in the junction area between the lid and baffle increases the overall flexibility of the earphone assembly 1 and reduces the pulling force exerted by the lid. The beveled edge may be easier to grip and more attractive.

Figure 20:
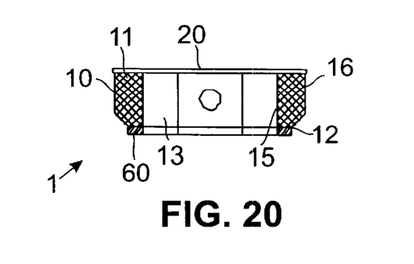
FIG. 20 is an end view in cut-away of an embodiment of the assembly of FIG. 1 wherein the lower, outer corner of the baffle is beveled.
Figure 21:
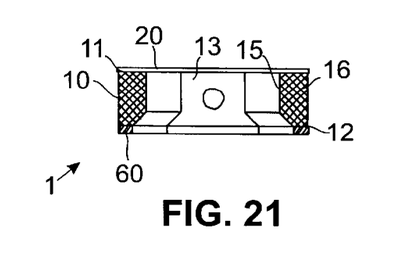
FIG. 21 is an end view in cut-away of an embodiment of the assembly of FIG. 1 wherein the inner, lower corner of the baffle is beveled.

Referring to FIG. 20, the corner of the baffle 10 formed by the outer wall 16 and the inner surface 12 of the baffle 10 is beveled. Referring to FIG. 21, the corner formed by the inner surface 12 and the inner wall 15 of the baffle is beveled. The beveling permits an increase in flexibility because the baffle is not connected to the skin of the patient over the entire thickness. The embodiments of FIGS. 20 and 21 maintain the acoustic benefits of the thicker wall while allowing for greater deformation of the baffle localized at the head contours.

Figure 22:
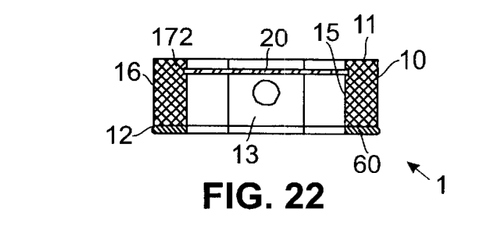
FIG. 22 is an end view in cut-away of an embodiment of the assembly of FIG. 1 wherein the lid is seated in a slot in the baffle.

The flexibility of the earphone assembly 1 may be increased by attaching the lid 20 to the baffle 10 in any manner that allows for some relative movement. Of course, the acoustic seal between the baffle and the lid is preferably maintained. Referring to FIG. 22, a slot 172 can be formed in the inner wall 15 of the baffle, proximate to the outer surface 11. The lid is seated in the slot. In this embodiment, adhesive is not required to secure the lid to the baffle which can simplify manufacturing. Further, the lid is not fixed to the entire surface of the baffle. The baffle is thus free to "roll" about the edge of the lid, as well as to compress and elongate. Further, to a limited extent, the lid can slide within the slot, increasing the permissive relative movement. Alternatively, the lid can be simply pressed into the chamber 13 and maintained in position by friction with the inner wall 15.

Figure 23:
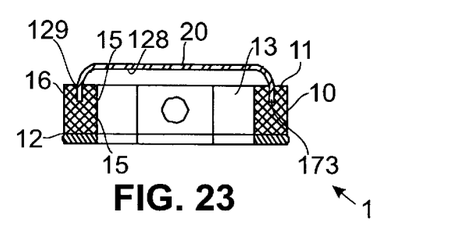
FIG. 23 is an end view in cut-away of an embodiment of the assembly of FIG. 1 wherein the lid has a cup shape and is seated in a slot in the baffle.
Figure 24:
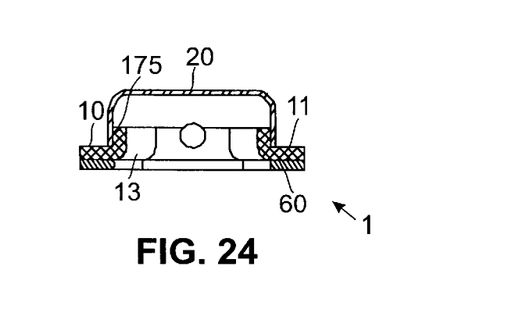
FIG. 24 is an end view in cut-away of an embodiment of the assembly of FIG. 1 wherein the lid has a cup shape and is seated on a shoulder on the baffle.

Referring to FIGS. 23 and 24, the lid 20 may have a cup-shape with a concave surface 128. The edge 129 of the lid thus forms a lip that is attached to the baffle 10. Referring to FIG. 23, a slot 173 is disposed in the outer surface 22 of the baffle. The lip is seated in the slot. An adhesive is employed to secure the lid to the baffle. Referring to FIG. 24, the baffle is formed with an external step 175 and flange 275. The flange may be oversized, creating a greater adhesive area. The lid 20 is sized to enclose the step. An adhesive may be employed to secure the lid to the baffle. The lip may be contoured to approximate the contour of the typical patient's head, reducing the flexibility demanded of the lid and the baffle.

Figure 25:
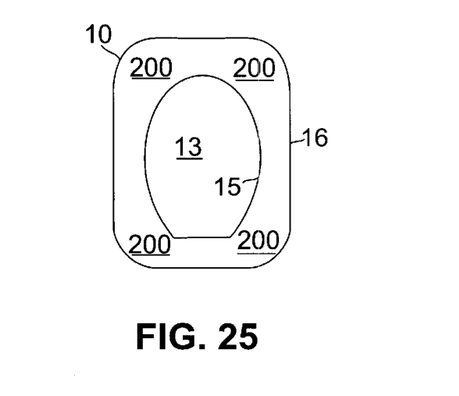
FIG. 25 is a top view of a baffle with a rectangular exterior wall.
Figure 26:
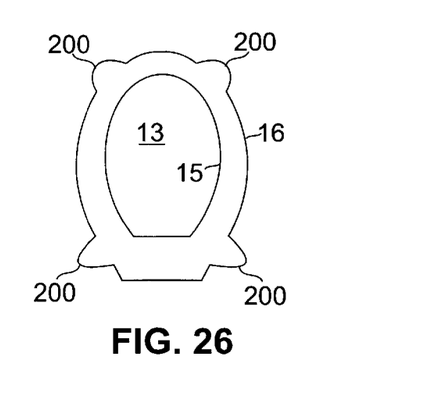
FIG. 26 is a top view of a baffle with tabs.

Referring to FIG. 25, another embodiment of the invention is disclosed. The exterior wall 16 of the baffle 10 has a rectangular shape. The rectangular shape may be particularly advantageous when manufacturing the earphone assembly 1 since the rectangular shape is readily manipulated by pick-and-place machinery. The interior wall 15 has a generally oval shape. This configuration creates tabs 200 at the corners of the baffle 10. The tabs increase to total surface area (and thus adhesive) in contact with the skin of the patient. This increased adhesive area is concentrated at the corners where severe contours are more likely to found. Referring to FIG. 26, this effect can also be achieved by attaching tabs at the corners of the exterior wall of the baffle. The additional adhesive on the tabs further secures the baffle to the patient's head without greatly increasing the foam mass of the baffle (and thus the rigidity of the earphone assembly 1).

The various cuts 71–80, 129, 170–172, and 176–178 in the baffle 10 can be formed in various ways. In particular, the foam baffle can be formed in a traditional manner and the cuts made (using a knife-edge, punch, or similar cutting device) in the formed baffle. Alternatively, the baffle can be formed in a mold such that the cuts are positioned in the baffle as formed. Using a mold to crate the cuts in the baffle would require reduced manufacturing costs but the mold would be more expensive. Further, there would be less design flexibility in the placements of the cuts. Of course, a combination of a mold forming certain cuts in the baffle with the later addition of other cuts appropriate for a particular application can be employed. For example, a mold may be employed to form a baffle including a circumferential cut, such as s cut 73 shown in FIG. 5, and a gouge 171 shown in FIG. 17. Later, tangential cuts, such as cuts 77 shown in FIG. 7 may added. The tangential cuts can be positioned based, at least in part, on the contours of the patient's head. The earphone assembly 1 of the instant invention may be employed with a transducer (not shown), a portion of which passes through aperture 180 into central chamber 13 (see FIGS. 1 and 2). The aperture 180 may be located in a location that is different from what is illustrated in the drawings. The transducer may have a ribbed cylinder to provide an airtight friction-fit to the inside of aperture 180. In this regard, aperture 180 is preferably circular in cross-section and cylindrical. A suitable transducer is the product known as the Acoustic Transducer Assembly, part no. 040176, available from Natus Medical Incorporated, San Carlos, Calif., the assignee hereof, and sold for use with the ALGO™ Series of hearing screening instruments, also available from Natus Medical. It should be understood that aperture 180 may have any shape that will couple securely, tightly, and removably to a transducer. Although the transducer forms no part of the present invention, it is contemplated that the length of the aperture 180 be shorter than the portion of the transducer that is inserted into aperture 180. This, advantageously, allows inspection of the transducer to verify non-obstruction.

A U-shaped projection may be supplied proximate to aperture 180 which projects from flattened end 14 to engage the transducer and minimize the rotation of the transducer in use, e.g., as a result of patient movement. It should be understood that in place of the U-shaped projection, a flange, a plurality of flanges, or a pin and hole assembly, or some other well-known, device for engaging a transducer to minimize rotation relative to baffle 10, may be used.

Uncertainty in the results of testing may arise if the transducer and the earphone assembly are incompatible. To encourage compatibility, the aperture or port 180 may be provided with a proprietary interface that is designed to engage and cooperate with a specific transducer. The aperture has a unique cross-section or size, which matches only a given transducer, similar to a key/lock assembly. Preferably, the cross-section of the aperture and the transducer is non-circular. Alternatively, a computer chip or other signal device may be incorporated into the baffle, which sends a signal identifying the earphone assembly. The transducer is provided with a signal reading device designed to receive the signal from the baffle signal device. The transducer would then modify its acoustic energy delivery in view of the design of the particular earphone assembly. If an unrecognized signal is received, a controller in the transducer could prevent the delivery of acoustic energy at all. In this way, the delivered acoustic energy would be appropriate for the given earphone assembly and the use of unverified components (and their associated dangers) can be prevented.

The adhesives used in the earphone assembly 1 are preferably pressure sensitive and approved for medical applications. The adhesive is selected to have at least enough strength to stick to the patient's head, creating an air-tight seal, for hearing screening, yet be weak enough for easy removal of the baffle 10 from engagement with the patient's head without trauma to the patient. In addition, the adhesive should be strong enough to create an acoustically tight seal between the baffle 10 and the lid 20. Various transfer adhesives may be employed. In particular, suitable adhesives include a hydrogel, such as adhesive product #63B distributed by Promeon (preferred for use on the inner surface 12), and acrylic (acrylate), for example, double coated medical tapes and transfer adhesives such as product numbers 1522, 9874, 1524, and 9879, (preferred for use on outer surface 11) each of which is available from 3M Health Care, St. Paul, Minn. These tapes may be transparent polyethylene coated films or polyester fiber based tapes which are generally sold with one side covered by a silicone treated Kraft-Glassine paper liner. Of course, acrylic or other adhesives well-known in the art can be employed and practice the invention.

The baffle 20 is preferably constructed of a resilient open-celled foam, in which air is blocked from freely moving from one side of the foam to the other due to the tortuous paths formed by the open cell structure of the foam. The adhesive coatings on the two sides enhance the air impermeability. The open cell foam also is resilient and provides comfort and easy conformability to the patient's head. The opened-cell foam may be any that is conventional in the art, for example, polyvinylchloride (PVC) foam. Closed-cell foam may also be employed as the baffle 20, whereby air cannot pass through the foam. Suitable closed-cell foam may be polyethylene foam. Thus, by the use of a foamed baffle 20, the amount of ambient noise capable of passing through the earphone assembly 1 is minimized.

It will be appreciated that the present invention may be used with conventional hearing screening equipment as is well known in the art. For example, the models ALGO® Portable and ALGO® 2e hearing screening machines available from Natus Medical.

The present invention has been described in terms of the preferred embodiments of the invention, which are presented for purposes of illustration and not of limitation. The present invention has several advantages over the prior art including that it is easily manufactured, cost-effective, and automatically adjusts to heads of various contours.

Moreover, the earphone of the present invention is simple, lightweight, and safe for use with infants. It will be appreciated that modifications, variations, and features within the scope of the invention, given the benefit of the disclosure, will occur to one of ordinary skill in the art. In particular, the various cuts and hinges disclosed herein can be combined and arranged in different manners depending upon the given application, testing regimen and the particular patient's head.

We claim:

1. An earphone comprising:
    an annular baffle including an outer surface and an inner surface separated by a height, and an interior wall and an exterior wall separated by a thickness, the interior wall defining a central chamber;
    a transparent, flexible lid attached to the baffle along the outer surface, completely covering the central chamber and forming an acoustic seal with the baffle, the lid having an inner face and an outer face;
    at least one radial cut in the annular baffle extending at least partly through the annular baffle;
    at least one circumferential cut extending at least partly through the thickness of the annular baffle from the inner surface and disposed between the exterior wall and the interior wall;
    at least one hinge disposed on the flexible lid;
    tabs mounted to the exterior wall wherein at least one surface of the tabs is aligned with the inner surface of the baffle; and
    an adhesive material applied to the inner surface of the annular baffle and to the tabs.

2. An earphone assembly for use with a transducer for hearing screening comprising:
    an annular baffle including an outer surface and an inner surface separated by a height, the baffle defining a central chamber;
    a flexible lid attached to the baffle along the outer surface and covering the central chamber, wherein an acoustic seal is formed between the lid and the baffle; and
    a port through the baffle to the central chamber for conveying acoustic energy to and from the chamber.

3. The earphone assembly of claim 2 wherein the flexible lid includes an inner face and an outer face, further comprising a hinge disposed along a face of the flexible lid and wherein an acoustic seal is formed between the inner face of the lid and the outer surface of the baffle.

4. The earphone assembly of claim 3 wherein the hinge is a groove disposed in the outer face of the flexible lid.

5. The earphone assembly of claim 2 wherein the lid includes an inner face and outer face and further comprising a plurality of hinges disposed in the outer face of the lid.

6. The earphone assembly of claim 5 wherein at least two of the hinges intersect.

7. The earphone assembly of claim 6 wherein at least two of the hinges intersect at an angle of about 70°.

8. The earphone assembly of claim 2 wherein the flexible lid is transparent and further comprising a target on the lid.

9. The earphone assembly of claim 3 wherein the annular baffle includes a first upper quadrant, a second upper quadrant, a first lower quadrant and a second lower quadrant, and wherein the hinge extends generally from the first upper quadrant to the second lower quadrant.

10. The earphone assembly of claim 9 further comprising at least two hinges extending parallel to each other.

11. The earphone assembly of claim 2 further comprising at least one cut in the annular baffle extending from the inner surface at least partly through the height of annular baffle.

12. The earphone assembly of claim 11 wherein the annular baffle is comprises four contiguous quadrants and cuts are positioned between at least three quadrants, extending radially outward from the central chamber.

13. The earphone assembly of claim 2 wherein the annular baffle has an exterior wall and an interior wall separated by a thickness, further comprising a circumferential cut extending at least partly through the thickness of the annular baffle from the inner surface and disposed between the exterior wall and the interior wall.

14. The earphone assembly of claim 13 further comprising radial slits extending at least partly through the annular baffle.

15. The earphone assembly of claim 2 wherein the annular baffle further comprises an interior wall defining the central chamber, and an exterior wall, the assembly further comprising tabs mounted to the exterior wall and an adhesive applied to the inner surface of the annular baffle and the tabs.

16. The earphone assembly of claim 2 wherein the annular baffle further comprises an interior wall with an oval shape defining the central chamber, an exterior wall having a rectangular shape and an adhesive applied to the inner surface of the annular baffle.

17. An earphone assembly for use during hearing screening comprising:
    a baffle forming a closed loop and defining a central chamber, the baffle having an inner surface, and outer surface, an interior wall and an exterior wall;
    a lid attached to the outer surface of the baffle; and
    a means for conveying sound to the central chamber disposed in the wall; and
    at least one cut disposed in the baffle.

18. The earphone assembly of claim 17 wherein the cut comprises at least one slit disposed along the exterior wall of the baffle, extending circumferentially about the baffle.

19. The earphone assembly of claim 17 wherein the cut is disposed along the interior wall of the baffle, extending circumferentially about the central chamber.

20. The earphone assembly of claim 17 wherein the cut extends radially from the interior wall to the exterior wall.

21. The earphone assembly of claim 17 further comprising tabs mounted to the exterior wall.

22. The earphone assembly of claim 17 further comprising a means for increasing the flexibility of the lid.

23. The earphone assembly of claim 22 wherein the flexibility increasing means comprises at least one hinge disposed on the lid.

24. The earphone assembly of claim 23 wherein the hinge is a groove extending from the first upper portion of the wall to the second lower portion of the wall.

25. The earphone assembly of claim 22 wherein the flexibility increasing means comprises a plurality of grooves disposed on the lid, the lid is made of a substantially transparent material and the grooves form a visible grid.

26. The earphone assembly of claim 17 further comprising a slot disposed along an interior wall of the baffle extending circumferentially about the central chamber, wherein the lid is seated on the slot.

27. The earphone of claim 17 further comprising a visible translucent target on the lid.

28. The earphone of claim 17 wherein the cut comprises a circumferential cut extending at least partly through the thickness of the annular baffle from the inner surface and disposed between the exterior wall and the interior wall.

29. The earphone of claim 28 wherein the cut comprises radial slits extending at least partly through the annular baffle.

30. The earphone of claim 29 wherein a first set of radial slits extend from the inner wall to the circumferential cut and a second set of radial slits extend from the circumferential cut to the outer wall.

31. The earphone of claim 30 wherein the first set of radial slits are offset from the second set of radial slits.

32. The earphone assembly of claim 17 wherein the lid has an edge which is disposed on the outer surface between the interior wall and the exterior wall.

33. The assembly earphone of claim 17 wherein a corner formed by the outer surface and the exterior wall is beveled.

34. The earphone assembly of claim 17 wherein a corner formed by the inner surface and the exterior wall is beveled.

35. The earphone assembly of claim 17 wherein a corner formed by the inner surface and the interior wall is beveled.

36. An earphone assembly comprising:
    a baffle forming a closed loop and having an inner surface, and outer surface, an interior wall, an exterior wall, a thickness extending from the interior wall to the exterior wall and a height extending from the inner surface to the outer surface;
    wherein a central chamber having an oval shape is defined by the interior wall;
    a flexible lid attached to the outer surface of the baffle, covering the central chamber and forming an acoustic seal with the outer surface of the baffle; and
    a means for conveying sound to the central chamber disposed in the baffle; and
    a cut disposed in the baffle.

37. The earphone assembly of claim 36 wherein the lid is cup-shaped with a concave surface surrounded by a lip, and wherein the lip is attached to the outer surface of the baffle by an adhesive such that the concave surface faces the baffle.

38. The earphone assembly of claim 37 further comprising a slot disposed in the outer surface of the baffle, wherein the lip is seated in the slot.

39. The earphone assembly of claim 37 further comprising a step formed in the outer surface of the baffle wherein the lip is seated snugly about the step.

40. An earphone for attachment to skin of a patient undergoing hearing screening comprising:
    an annular baffle including an outer surface and an inner surface separated by a height, and an interior wall and an exterior wall separated by a thickness, the interior wall defining a central chamber;
    means for covering the chamber and forming an acoustic seal with the outer surface of the annular baffle;
    means for increasing the flexibility of the baffle;
    means for conveying acoustic energy to the chamber;
    means for increasing the flexibility of the covering means;
    means for forming an acoustic seal between the inner surface of the annular baffle and the skin of the patient.

41. The earphone of claim 40 wherein the baffle flexibility increasing means comprises at least one radial cut in the annular baffle extending at least partly through the annular baffle.

42. The earphone of claim 40 wherein the covering means comprises a lid and wherein the means for increasing the flexibility of the covering means comprises at least one groove disposed on the lid.

43. An earphone assembly comprising:
    a baffle forming a closed loop and having an inner surface, and outer surface, an interior wall, an exterior wall, a thickness extending from the interior wall to the exterior wall and a height extending from the inner surface to the outer surface;
    wherein a central chamber is defined by the interior wall;
    a flexible cup-shaped lid with a concave surface surrounded by a lip, wherein the lip is attached to the baffle such that the concave surface faces the baffle; and
    an apparatus for conveying sound to the central chamber disposed in the baffle.

44. The earphone assembly of claim 43 further comprising a slot disposed in the outer surface of the baffle, wherein the lip is seated in the slot.

45. The earphone assembly of claim 43 further comprising a step formed in the outer surface of the baffle wherein the lip is seated snugly about the step.

46. An earphone assembly for use with a transducer for hearing screening comprising:
    an annular baffle including an outer surface and an inner surface separated by a height, and an interior wall and an exterior wall separated by a thickness, the interior wall defining a central chamber;
    a lid attached to the baffle along the outer surface and covering the central chamber;
    an aperture through the baffle to the central chamber for conveying acoustic energy to the chamber; and
    tabs attached to the exterior wall of the annular baffle.

47. An earphone assembly for use with a transducer for hearing screening comprising:
    an annular baffle including an outer surface and an inner surface separated by a height, and an interior wall and an exterior wall separated by a thickness, the interior wall defining a central chamber;
    a transparent lid attached to the baffle along the outer surface, completely covering the central chamber and forming an acoustic seal with the baffle, the lid having an inner face, an outer face and an edge;
    at least one cut in the annular baffle extending at least partly through the annular baffle; and
    an adhesive material applied to the inner surface of the annular baffle.

48. The earphone assembly of claim 47 further comprising a circumferential cut disposed in the outer surface of the annular baffle and disposed about the edge of the lid.

49. The earphone assembly of claim 47 further comprising a proprietary connection between the annular baffle and the transducer.

50. The earphone assembly of claim 47 further comprising a means for sending a signal identifying the baffle mounted in the baffle and a means reading the identifying signal operably engaged to the transducer to determine the identity of the baffle.

51. The earphone assembly of claim 50 further comprising a means for controlling the transducer based, at least in part, upon the identifying signal.

52. The earphone assembly of claim 50 wherein the identifying means comprises a computer chip mounted in the baffle.

53. The earphone assembly of claim 49 wherein the proprietary connection comprises an aperture in the baffle having a non-circular cross-section designed to match the non-circular cross-section of the transducer.

54. A method for assembling an earphone for use with a transducer for hearing screening comprising:
    providing an annular baffle including an outer surface and an inner surface separated by a height;
    defining a central chamber within the baffle;

attaching a flexible lid to the baffle along at least a portion of the outer surface forming an acoustic seal therebetween;

covering the central chamber with the flexible lid; and providing a port through the baffle to the central chamber for conveying acoustic energy to and from the chamber.

55. The method of claim 54 further comprising inserting cuts into the baffle.

56. The method of claim 54 further comprising providing hinges on the lid.

* * * * *